United States Patent
Gautieri

(10) Patent No.: US 8,806,916 B2
(45) Date of Patent: Aug. 19, 2014

(54) PHOTO-ACOUSTIC, MULTI-BAND, MULTI-CAVITY GAS DETECTION SYSTEM

(75) Inventor: Steven P. Gautieri, Gladstone, MO (US)

(73) Assignee: Honeywell International Inc., Morristown, NJ (US)

( * ) Notice: Subject to any disclaimer, the term of this patent is extended or adjusted under 35 U.S.C. 154(b) by 171 days.

(21) Appl. No.: 13/292,408

(22) Filed: Nov. 9, 2011

(65) Prior Publication Data

US 2013/0111975 A1    May 9, 2013

(51) Int. Cl.
  *G01N 21/00* (2006.01)
  *G01N 21/17* (2006.01)

(52) U.S. Cl.
  CPC .... *G01N 21/1702* (2013.01); *G01N 2021/1704* (2013.01)
  USPC .......................................................... 73/24.02

(58) Field of Classification Search
  CPC ...................... G01N 21/1702; G01N 29/2425
  USPC .......................................................... 73/24.02
  See application file for complete search history.

(56) References Cited

U.S. PATENT DOCUMENTS

| | | | | |
|---|---|---|---|---|
| 4,436,428 | A | * | 3/1984 | Watanabe et al. ............. 356/432 |
| 4,557,603 | A | * | 12/1985 | Oehler et al. ................. 356/418 |
| 2007/0151325 | A1 | * | 7/2007 | Kauppinen ................. 73/24.02 |

* cited by examiner

*Primary Examiner* — Peter Macchiarolo
*Assistant Examiner* — Alex Devito
(74) *Attorney, Agent, or Firm* — Husch Blackwell LLP

(57) ABSTRACT

A single gas detector combines a dual cavity photo-acoustic gas sensor with a common microphone and common source. Electrical outputs from the microphone can be analyzed to determine an analyte gas concentration in the local region being monitored. Radiant energy from the common source can be directed into both cavities simultaneously. Alternately, the sensor can be used with two microphones to establish a concentration of each of two different gasses, or a gas and water vapor.

16 Claims, 5 Drawing Sheets

PHOTO-ACOUSTIC, MULTI-BAND, MULTI-CAVITY GAS DETECTION SYSTEM

FIELD

The application pertains to gas detectors. More particularly, the application pertains to such detectors which include multiple absorption detection bands in a photo-acoustic-type detector. Ammonia is a very desirable refrigerant as its GWP (Global Warming Potential) is zero because of its very low narrow IR absorption characteristics. It is abundantly available, found all throughout nature, and extremely efficient in refrigeration systems requiring less energy to be utilized per BTU output. The low absorption property makes it difficult for conventional low-cost IR type gas detectors to accurately read and detect low-ppm levels.

BACKGROUND

Ammonia is the preferred low-cost environmentally friendly refrigerant used for most industrial food processes, cold storage, and pharmaceutical applications. Known commercially available ammonia detectors usually incorporate electrochemical sensor cells.

Currently Electrochemical cells are the most effective approach to monitoring low-level $NH_3$ levels. Cells are costly as they degrade over time requiring frequent replacement and the associated electronics add an additional cost and complexity to the sensor. Additionally, electrochemical cells have a limited life time as the electrolyte eventually dries up and this is accelerated in dry hot environments. Also, applications that have zero oxygen environments can't use most electrochemical cells for $NH_3$ detection as the electrolytes redox reaction requires $O_2$ to be present. The redox reaction within the electrolyte is also non-regenerative causing the constituents to be consumed that eventually cause the cell to stop functioning should a large $NH_3$ exposure occur, or if a small long-term background is present.

Additional applications where most electrochemical technology is not practical occur in chicken houses because of the constant background of $NH_3$ found in urine, live stock indoor air quality control because of the constant background of $NH_3$ in urine, dry/hot conditions. "Zero Oxygen" applications commonly found in fruit cold storage. Fruit storage or any environment requiring oxygen to be displaced using $CO_2$ or $N_2$ filled rooms to delay fruit ripening doesn't allow electrochemical cells to detect ammonia. Solar panel manufacturing also requires some oxygen to be displaced to reduce spontaneous explosions from chemicals used in the manufacturing process.

Another problematic issue with electrochemical cells is the destruction of the electrolyte and the internal electrodes within the cell when exposed to VOC evaporates. A multitude of cleaning and solvent chemicals can destroy the integrity of most electrochemical cells slowing the response to $NH_3$ down or cause the cell to no longer detect $NH_3$. This creates a safety hazard as there would not be sufficient time to warn individuals near the sensor of the presence of $NH_3$ causing a safety hazard should an $NH_3$ leak occur.

Further, NDIR-type detectors that use the popular 3.3 µm band are costly and do not function as well because $NH_3$ has low IR absorption characteristics requiring high-gain sensitive components, highly polished surfaces, long path lengths, and complex precision optics. Ammonia has a very low absorption characteristic at this wavelength. In general, NDIR detectors are not as practical in ammonia gas detectors at the 3.3 µm, 10.4 µm, or 10.75 µm bands because the absorption bands very narrow, making it difficult to achieve stable signal levels for accurate detection readings near the 0-100 ppm range as the zero has a tendency to drift over time with this type of sensing technology. In addition, water vapor has IR absorption throughout the ammonia absorption spectra diluting signal levels and causing false alarms in wet humid environments. In a photo-acoustic system, the "zero" occurs naturally with no analyte present requiring minimal baseline signal correction compared to NDIR systems.

DETAILED DESCRIPTION

Figure 1:
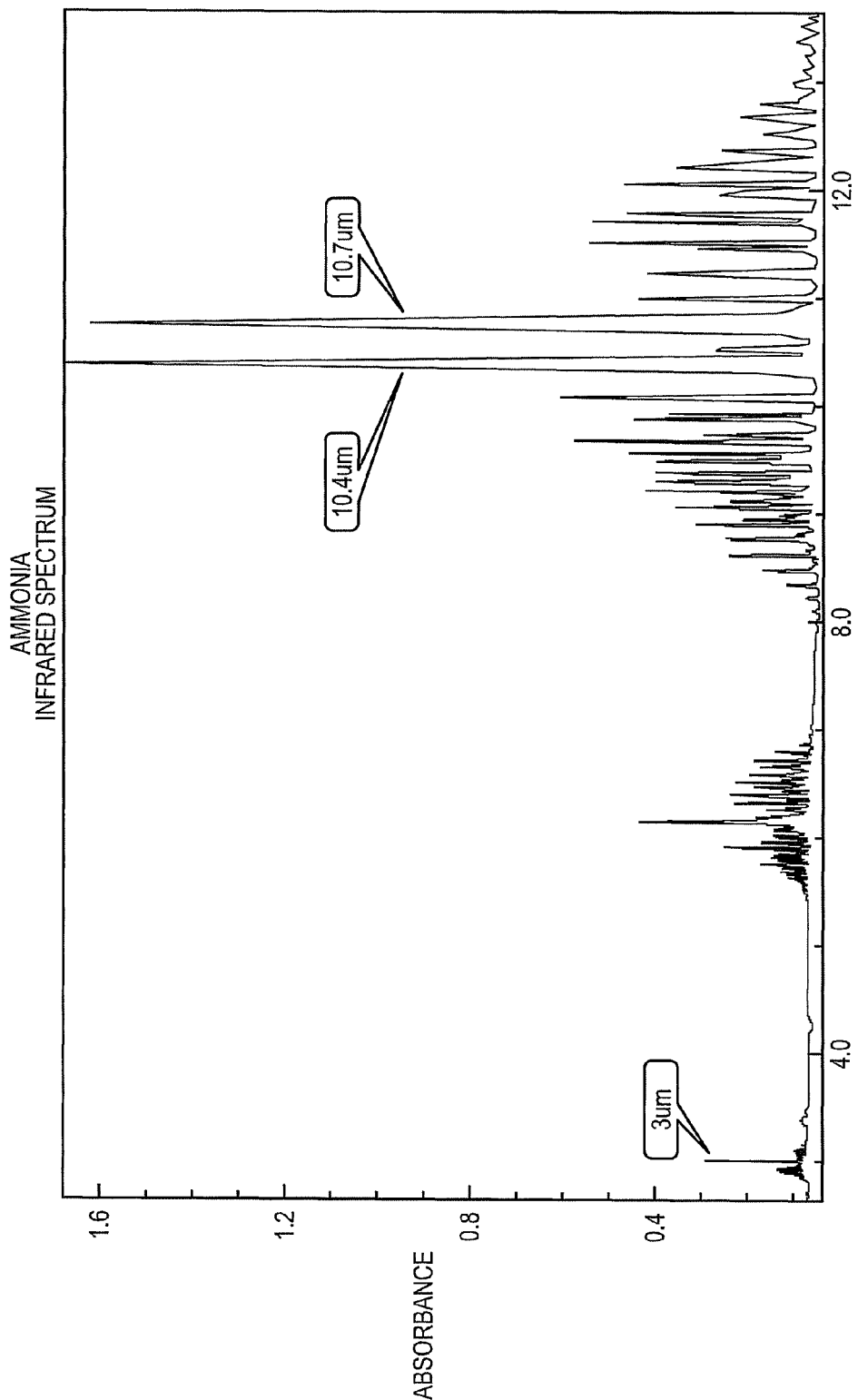
FIG. 1 is a graph illustrating absorption of ammonia at different wavelengths.

While disclosed embodiments can take many different forms, specific embodiments hereof are shown in the drawings and will be described herein in detail with the understanding that the present disclosure is to be considered as an exemplification of the principles hereof, as well as the best mode of practicing same, and is not intended to limit the claims hereof to the specific embodiment illustrated.

Embodiments hereof can implement multi-band multi-cavity photo-acoustic detectors which for example can utilize the two most intense absorption bands of $NH_3$ at 10.4 µm and 10.7 µm. verses the lower popular 3.3 µm single band for $NH_3$ gas detectors. $NH_3$ has a very low absorption characteristic.

In another embodiment, the disclosed approach could also monitor $H_2O$ vapor levels as they exist throughout the entire $NH_3$ absorption bands. Alternately, two different analyte gasses could be measured simultaneously using a single source.

FIG. 1 is a graph of $NH_3$ absorption spectra. It illustrates how much greater the absorption of $NH_3$ is in the 10 micron region compared to the 3 micron region. Thus, various substances, such as gasses, or water vapor can be detected using different absorption wavelengths.

When implemented to sense $NH_3$, the present photo-acoustic multi-band multi-cavity sensors include a photo-acoustic cavity for each of the two highest absorption bands; one at 10.4 µm and another at 10.75 µm. Advantageously, with the present multi-band multi-cavity structures, the absorption energy can be additive. This results in a greater signal-to-noise ratio for low $NH_3$ levels, hence, more accurate detection and lower LDL thresholds relative to known non-electrochemical technology detectors.

Figure 2:
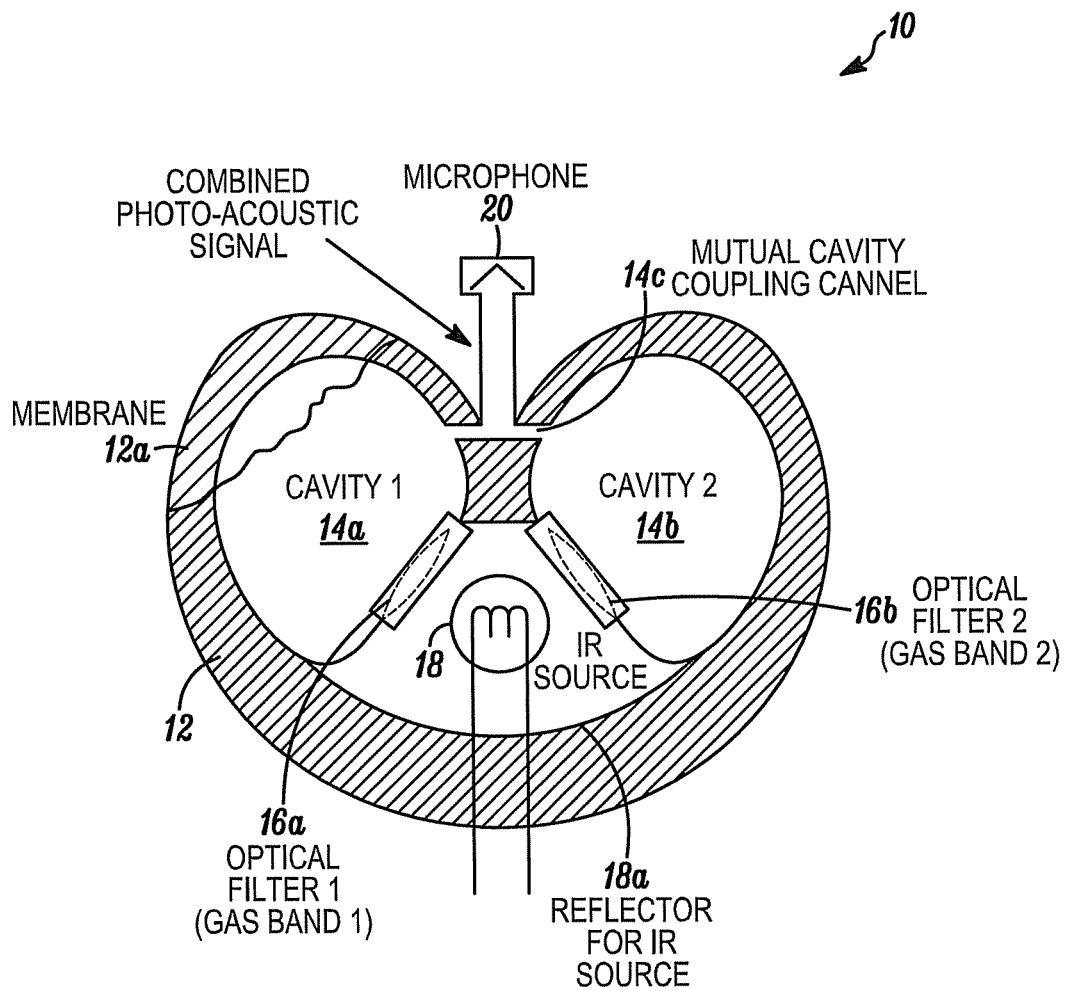
FIG. 2 is a diagram of a single microphone sensor in accordance herewith.
Figure 3:
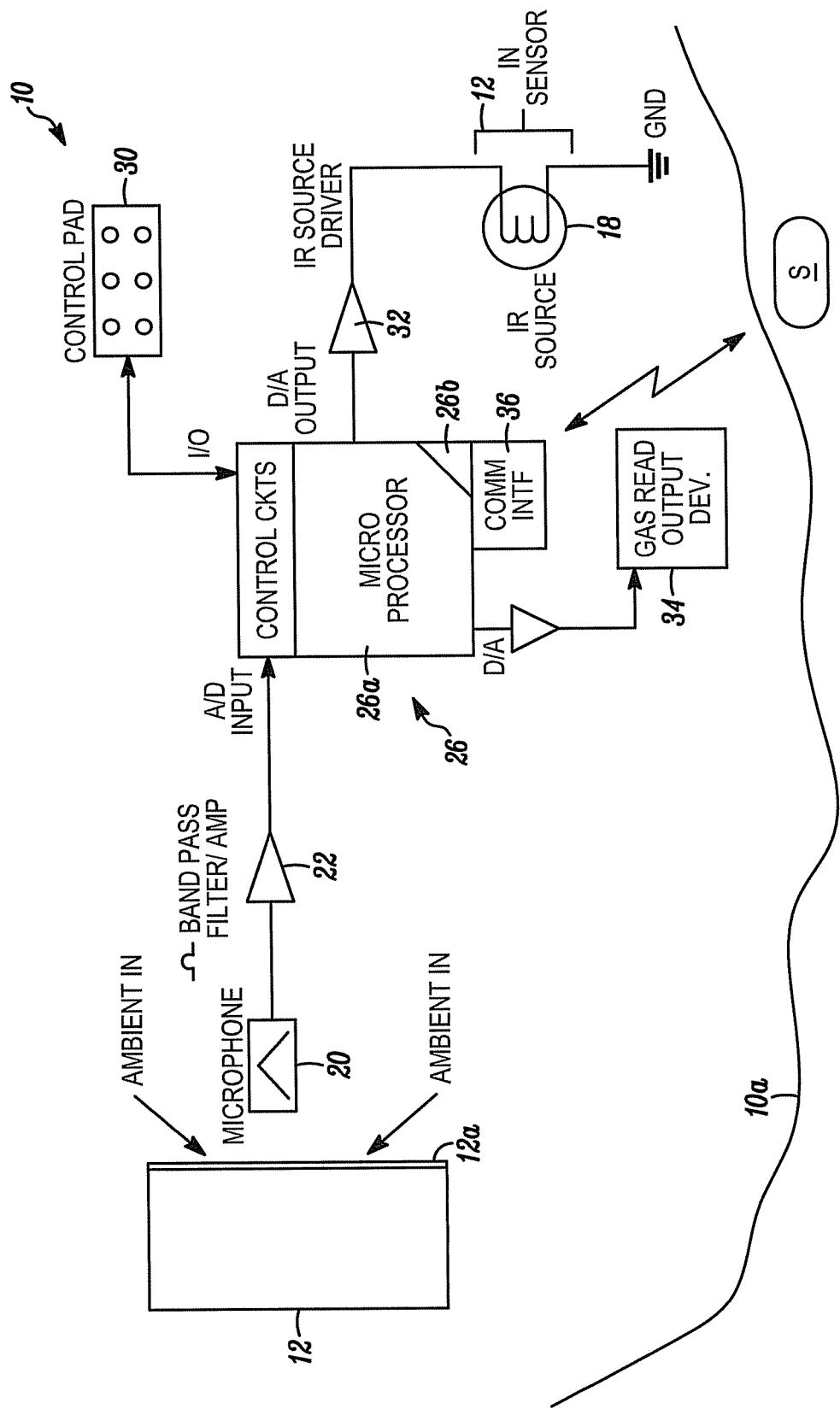
FIG. 3 is a block diagram of a single gas detector which incorporates the cavity of FIG. 2.

By way of example, with respect to FIGS. 2, 3 one embodiment would entail a single microphone and single source, with a mutually-coupled dual cavity. Each cavity is specific to one of multiple unique respective absorption band footprints of a single target gas. The photo-acoustic signal is combined from both cavities then coupled to a single microphone for an analyte gas measurement. This combined signal is stronger than the sum of individual signals which allow for weaker gas measurements because the signal to noise ratio is greater.

Without the ability to combine the PA signal from the two cavities two individual microphones would be required. This configuration would add noise to the overall signal readings and the increased number seals and port openings may increase leakage.

Use of one microphone in detectors of a single gas reduces background noise, pressure leakage, and volume required, allowing weaker signals to be detected. In the case for $NH_3$, given the weak absorption characteristics, this arrangement allows lower concentrations to be detected. With the low-concentration detection capability, the dual-cavity, single microphone approach would be a low-cost solution to electrochemical cells and costly NDIR to measure $NH_3$ or other difficult to detect gases. In addition, this solution would not degrade over time and the life expectancy would be years longer than the current life expectancy of electrochemical cells.

FIGS. 2, 3 disclose a single gas detector 10, with a housing 10a, configured with a sensor 12. The sensor 12 has first and second cavities 14a, b. Cavities 14a, b are covered by a common diffusion membrane 12a, shown partly broken away.

Optical filters 16a, b correspond to two different absorption bands 1, 2 for a selected gas, for example $NH_3$ and provide an optical input port to the respective cavities 14a, b.

An infrared source 18 is positioned adjacent to both of the filters 16a, b as a common source of radiant energy. A common microphone 20, coupled to the cavities 14a, b by a coupling channel 14c, additively receives acoustic signals indicative of the absorption from the cavities 14a, b. Output signals from the microphone 20, as best seen in FIG. 3, can be filtered, and/or shaped by an analog bandpass filter/amplifier 22.

Filtered outputs from filter/amplifier 22 are coupled to an input to control circuits 26. Control circuits 26 can include an analog-to-digital converter, and be implemented in part by a programmable processor 26a. Processor 26a can execute prestored instructions 26b in processing signals from the sensor 12.

Additional aspects of the detector 10 include a manually operable control pad 30, and a driver 32 coupled to the source 18 in sensor 12. A gas concentration readout device 34 can be coupled to the control circuits 26 along with a communications interface 36 which can communicate with a displaced monitoring system S via a wired or wireless medium.

Embodiments hereof include two adjoining cavities, such as 14a, b, combined with a common infrared source, such as 18, and, only one microphone, such as 20. Increased magnitudes of acoustic energy are additively sensed at the microphone 20 from two channels of absorption response. This results in an increased signal-to-noise ratio. Use of a single source reduces power requirements.

Sensors similar to sensor 12 can be used to simultaneously sense different substances such as two different gases, or a selected gas and water vapor. Again with reference to FIG. 1, a cavity can be irradiated at an $H_2O$ vapor band (outside of the absorption band for the selected gas) to compensate for variance in $H_2O$ vapor inside the absorption band of a selected gas.

One embodiment of a dual gas detector includes dual microphones, dual cavities, and a single source. Each cavity is specific to a selected target gas footprint absorption band. The photo-acoustic signal from each individual cavity is directed to a respective microphone for individual analyte gas measurement.

The above described embodiment allows multiple gasses to be simultaneously measured in one simple sensor configuration that utilizes common hardware. Two different gases can be detected simultaneously by use of a single source.

Utilizing a dual cavity sensor in combination with a single source reduces processing power requirements, and hardware costs. Examples include $CO_2$ and CO measurements which can be made simultaneously without the necessity for a multitude of individual gas sensors when multiple-gas sensing is required.

Figure 4:
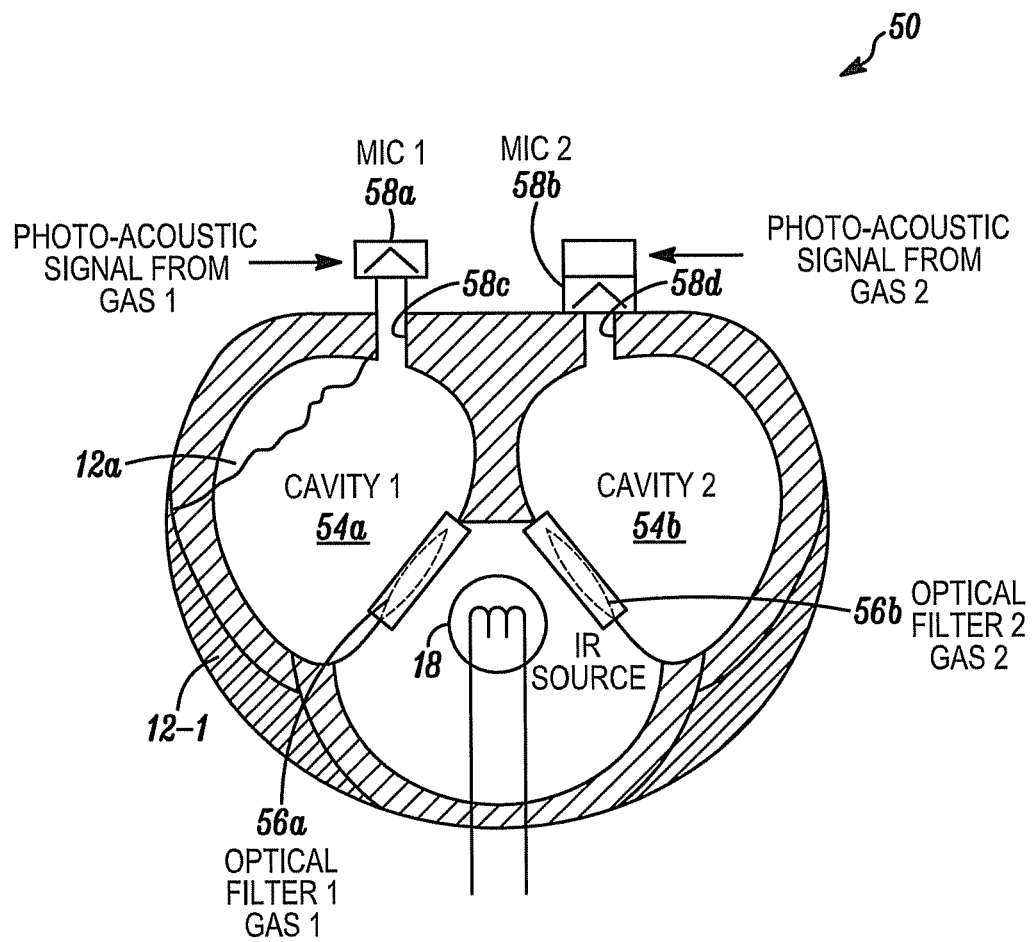
FIG. 4 is a diagram of a dual microphone sensor in accordance herewith.
Figure 5:
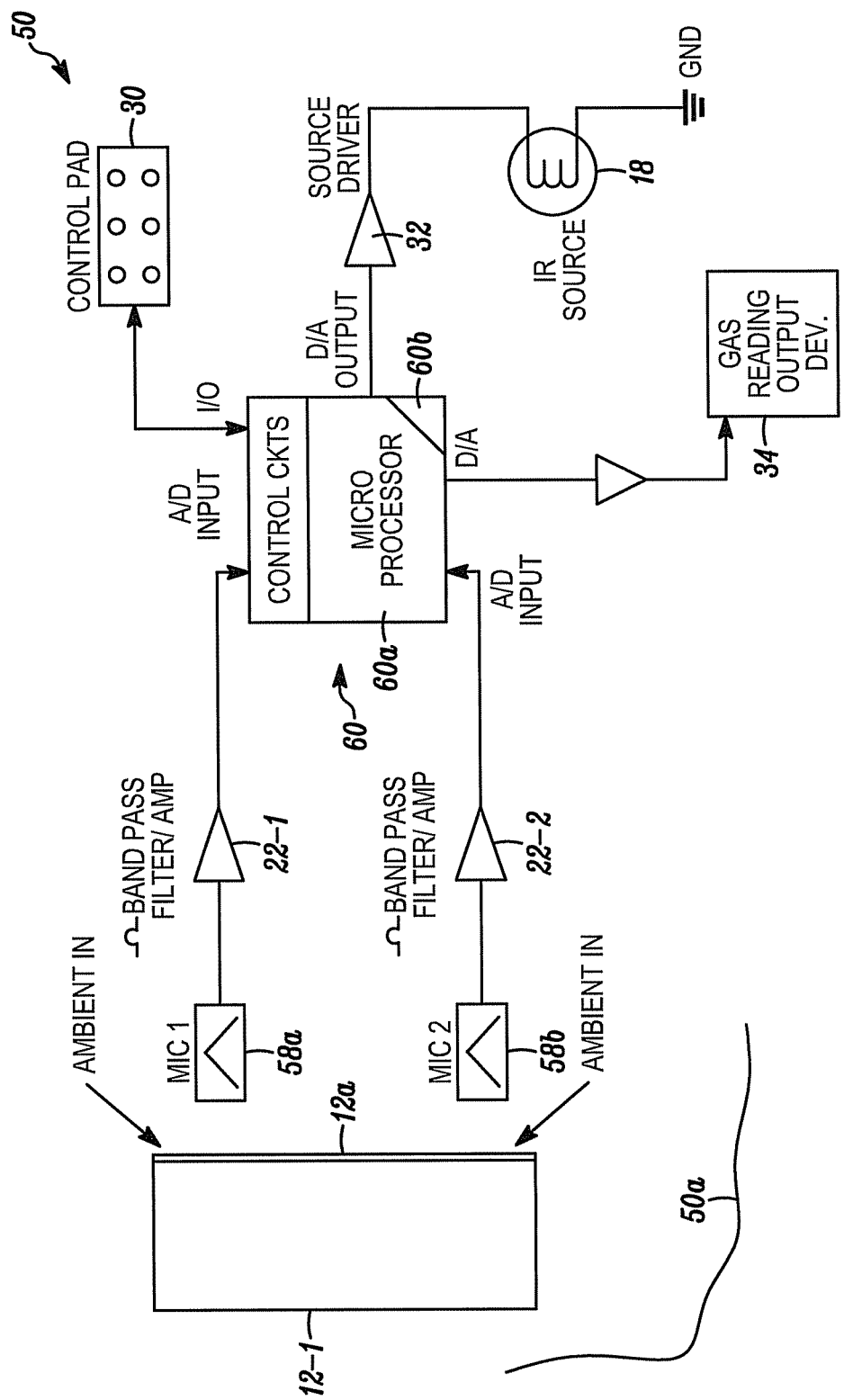
FIG. 5 is a block diagram of a detector of two different airborne gases, or one gas and water vapor.

FIGS. 4, 5 illustrate an exemplary multiple substance detector 50. Elements common to those in FIGS. 2, 3 have been given the same identification numerals as they were discussed above and need not be described further.

FIG. 4 discloses a detector 50, with a housing 50a, configured with a dual substance sensor 12-1. The sensor 12-1 has first and second cavities 54a, b. Cavities 54a, b are covered by a common diffusion membrane 12a, shown partly broken away.

Optical filters 56a, b correspond to two different absorption bands 1, 2 for two different selected gases, for example $CO_2$, CO and provide an optical input port to the respective cavities 54a, b.

An infrared source 18 is positioned adjacent to both of the filters 56a, b as a common source of radiant energy. First and second microphones 58a, b, are coupled to the respective cavities 54a, b by respective coupling channels 58c, d. The microphones 58a, b each receive acoustic signals indicative of the absorption from the cavities 54a, b. Output signals from the microphones 58a, b, as best seen in FIG. 5, can be filtered, and/or shaped by an analog bandpass filter/amplifiers 22-1, 22-2.

Filtered outputs from filter/amplifiers 22-1, -2 are coupled to inputs to control circuits 60. Control circuits 60 can include analog-to-digital converters, and be implemented in part by a programmable processor 60a. Processor 60a can execute pre-stored instructions 60b in processing signals from the sensor 12-1.

Additional aspects of the exemplary detector 50 include a manually operable control pad 30, and a driver 32 coupled to the source 18 in sensor 12-1. A gas concentration readout device 34 can be coupled to the control circuits 26 along with a communications interface 36 which can communicate with a displaced monitoring system S via a wired or wireless medium.

In yet another embodiment, water vapor can be sensed and measured. Water vapor is very problematic when attempting to measure a multitude of gasses as water vapor is present over most of the refrigerant band and can cause false readings and humidity signal errors, can be measured. For example, in circumstances where water vapor exists in the analyte absorption band, one cavity can respond to the water vapor absorption band and the other cavity can respond to the target gas absorption band.

The water vapor signal is then subtracted from the analyte gas signal to produce a gas concentration parameter without water vapor cross sensitivity which results from humidity variations. The water vapor cavity can also be used as a reference cavity for ambient noise cancelation in a dual microphone configuration.

Those of skill will recognize that multi-substance sensors in accordance herewith can have a variety of physical configurations. All such configurations fall within the spirit and scope of this application.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

Further, logic flows depicted in the figures do not require the particular order shown, or sequential order, to achieve desirable results. Other steps may be provided, or steps may be eliminated, from the described flows, and other components may be add to, or removed from the described embodiments.

The invention claimed is:

1. A photo-acoustic gas detector comprising:
a sensor having first and second, spaced apart gas absorption cavities;
at least one microphone coupled acoustically to at least one of the cavities;
a common source of radiant energy coupled optically to the two cavities, and which injects radiant energy into both of the cavities; and
control circuits coupled to the microphone to establish at least one gas concentration, associated with at least one of the cavities,
wherein different acoustic signals from each cavity are combined together to form a composite acoustic signal before the composite acoustic signal is coupled to the microphone for measurement,
wherein the control circuits establish the gas concentration in response to the measurement of the composite acoustic signal by the microphone, and
wherein the composite acoustic signal is stronger than a sum of the different acoustic signals from each cavity.

2. A detector as in claim 1 with an optical filter associated with each cavity and where the filters have different center wavelengths.

3. A detector as in claim 2 where the control circuits are coupled to the common source.

4. A detector as in claim 1 which includes a housing which carries the sensor including two optical filters with the common source adjacent to the two filters.

5. A detector as in claim 1 which includes two microphones, with a microphone associated with each cavity.

6. A detector as in claim 5 which includes separate signal processing channels for each microphone.

7. A detector as in claim 5 where the control circuits evaluate a substance concentration associated with an absorption characteristic of each cavity.

8. A detector as in claim 7 where the control circuits compensate signals from each cavity with the signal associated with the other cavity.

9. A method of determining concentration of a sample comprising:
generating a first audio indicator of absorption of radiant energy by the sample at a first wavelength;
generating a second audio indicator of absorption of radiant energy by a different sample at a second wavelength;
combining the first and second audio indicators to form a composite acoustic signal;
after forming the composite acoustic signal, coupling the composite acoustic signal to a microphone for measurement of the composite acoustic signal; and
responsive to the measurement of the composite acoustic signal, generating an electrical signal indicative of the substance concentration of at least one sample,
wherein the composite acoustic signal is stronger than a sum of the sensed audio indicators.

10. A method as in claim 9 which includes originating common radiant energy, and, directing radiant energy at the samples at first and second, different wavelengths.

11. A method as in claim 9 which includes using the composite acoustic signal in determining a gas concentration.

12. A method as in claim 9 which includes sensing an audio indictor of absorption of radiant energy by a selected vapor and generating an electrical signal responsive to all sensed audio indicators.

13. A method as in claim 11 which includes compensating the electrical signal by incorporating absorption of radiant energy by a selected vapor.

14. A method as in claim 10 which includes providing a sample sensing cavity associated with each of the wavelengths.

15. A method as in claim 14 which includes providing a vapor sensing cavity associated with one of the wavelengths.

16. A dual channel photo-acoustic gas detector comprising:
first and second gas sensing cavities;
a common microphone to measure acoustic signals; and
a common source of radiant energy which can be directed into both cavities,
wherein the acoustic signals from both cavities are combined to form a composite acoustic signal before the composite acoustic signal is coupled to the microphone for measurement,
wherein electrical outputs from the microphone are analyzed to determine a gas concentration in the cavities, and
wherein the composite acoustic signal is stronger than a sum of the acoustic signals from both cavities.

* * * * *